(12) United States Patent
Malthe-Sorenssen et al.

(10) Patent No.: US 6,337,422 B1
(45) Date of Patent: Jan. 8, 2002

(54) YELLOW POLYMORPH OF 5-AMINO-2,4,6-TRIIODO-N,N'-BIS(2-3-DIHYDROXYPROPY)-ISOPHTHALAMIDE

(75) Inventors: Dick Malthe-Sorenssen, Spangereid; Audun Aukrust, Oslo, both of (NO)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/438,385

(22) Filed: Nov. 12, 1999

Related U.S. Application Data

(63) Continuation of application No. PCT/GB98/01492, filed on May 22, 1998.
(60) Provisional application No. 60/049,176, filed on Jun. 10, 1997.

(30) Foreign Application Priority Data

May 23, 1997 (GB) ................................................ 9710726

(51) Int. Cl.$^7$ ............................................. C07C 233/05
(52) U.S. Cl. ..................................... 564/153; 424/9.452
(58) Field of Search ........................ 564/153; 424/9.452

(56) References Cited

FOREIGN PATENT DOCUMENTS

GB        1 548 594 A        7/1979

OTHER PUBLICATIONS

Haavaldsen et al, Acta Pharm. Suec., 20, 219–232, 1983.*

* cited by examiner

*Primary Examiner*—Shailendra Kumar
(74) *Attorney, Agent, or Firm*—Bacon & Thomas

(57) ABSTRACT

The yellow polymorph of 5-amino-2,4,6-triiodo-N,N'-bis(2,3-dihydroxypropyl)-isophthalamide is described.

5 Claims, 6 Drawing Sheets

IR OF THE YELLOW POLYMORPH

IR OF THE WHITE POLYMORPH

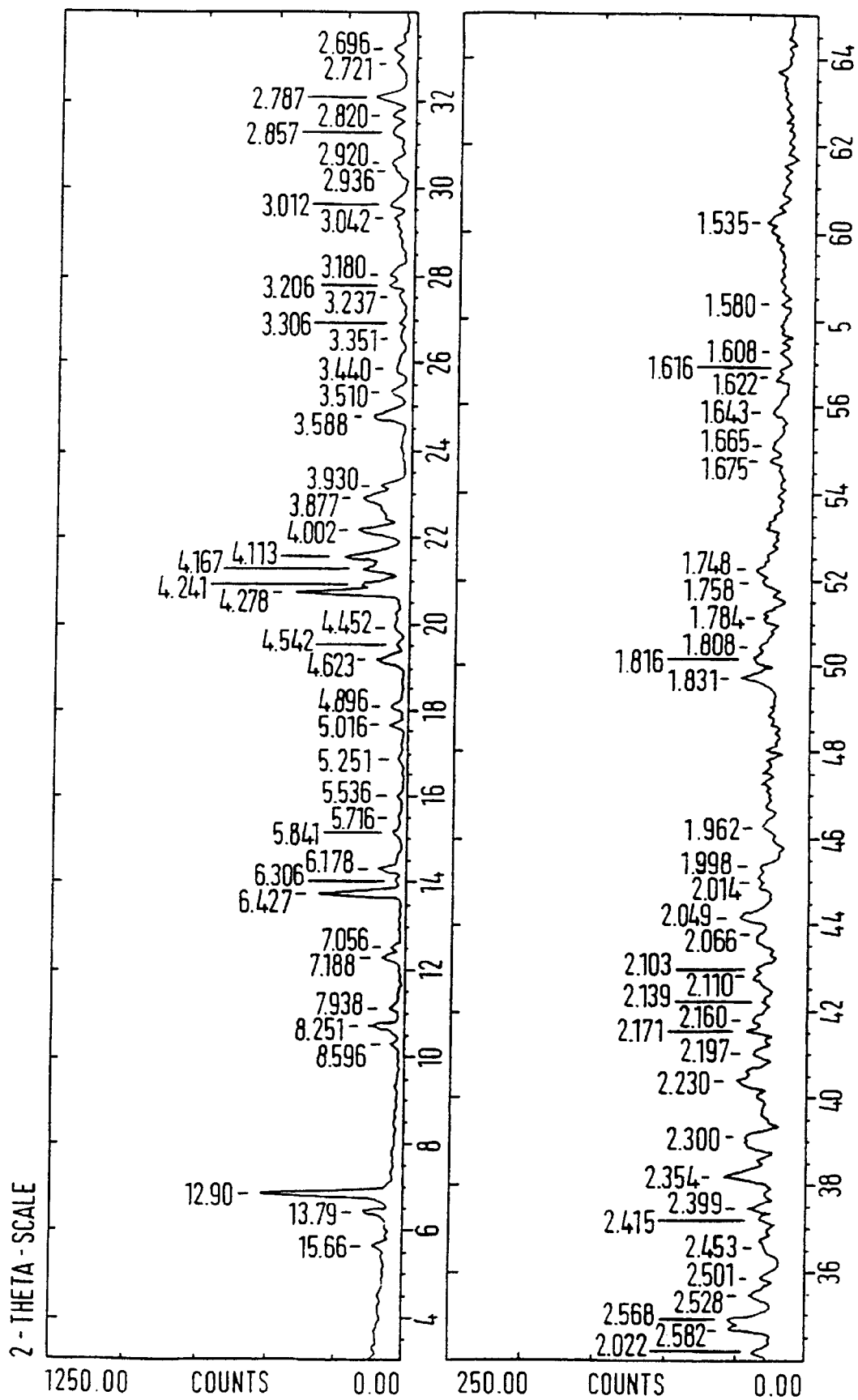
FIG. 3 POWDER X-RAY OF THE YELLOW POLYMORPH

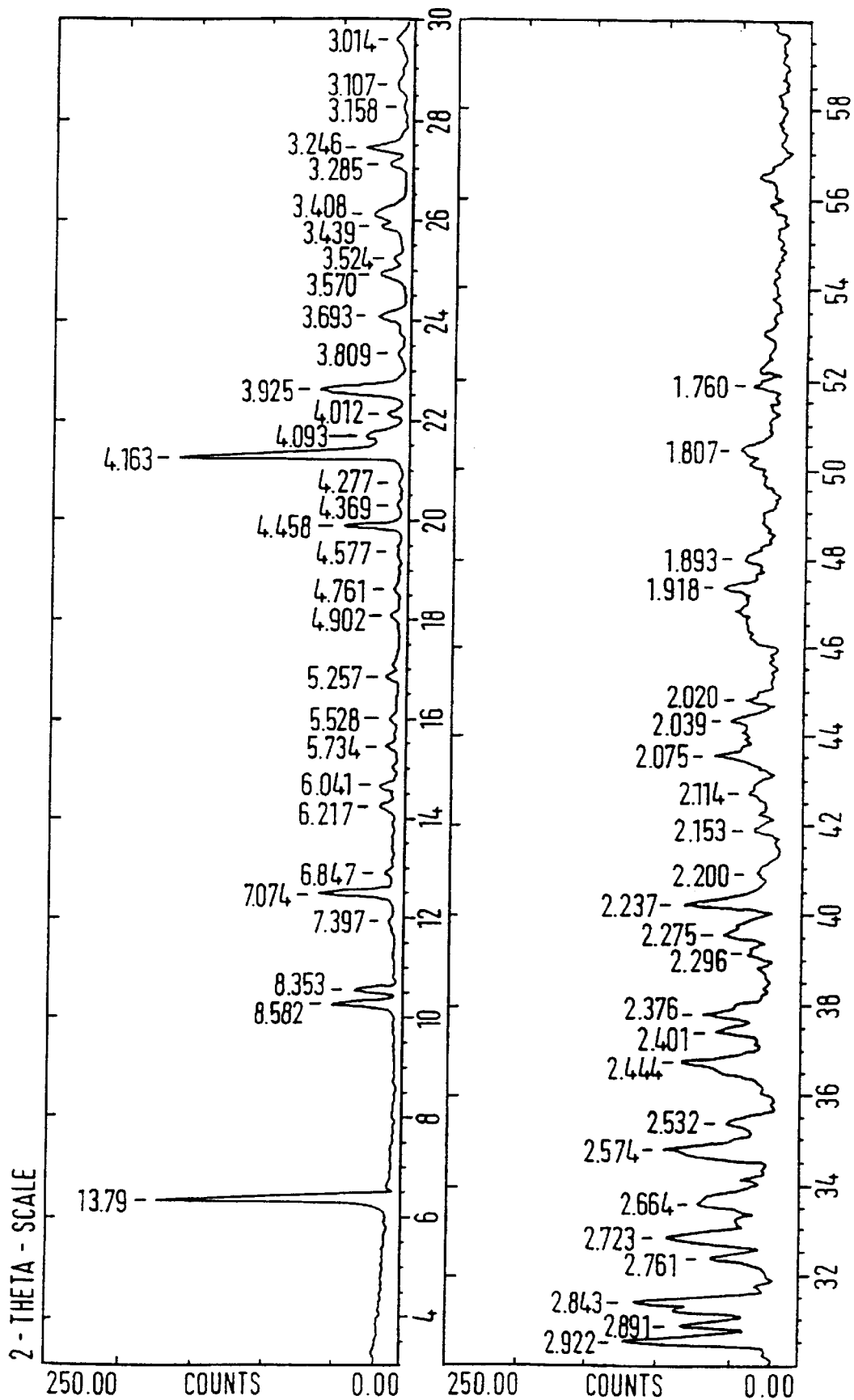
FIG. 4 POWDER X-RAY OF THE WHITE POLYMORPH

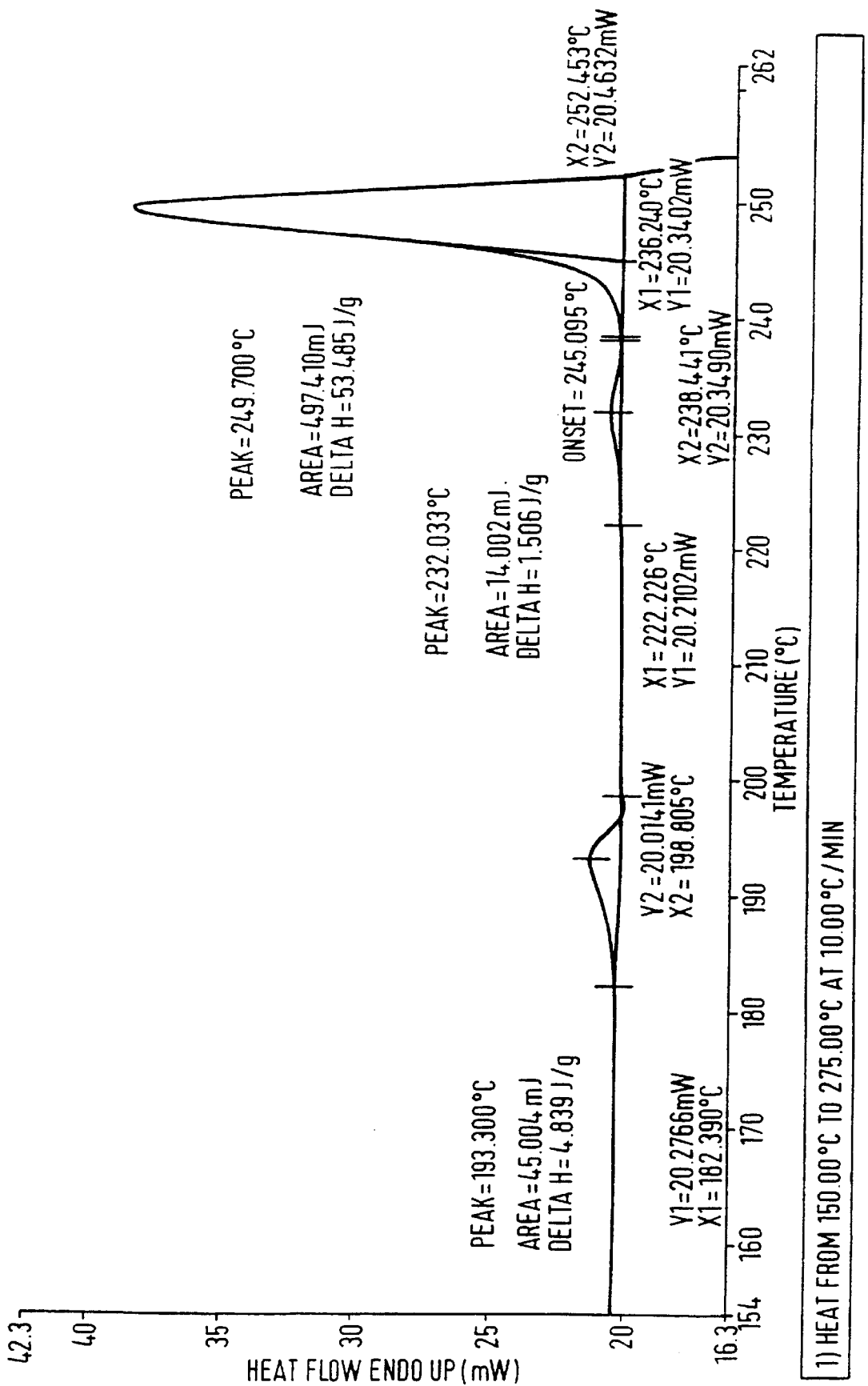
FIG. 5 DSC OF THE YELLOW POLYMORPH

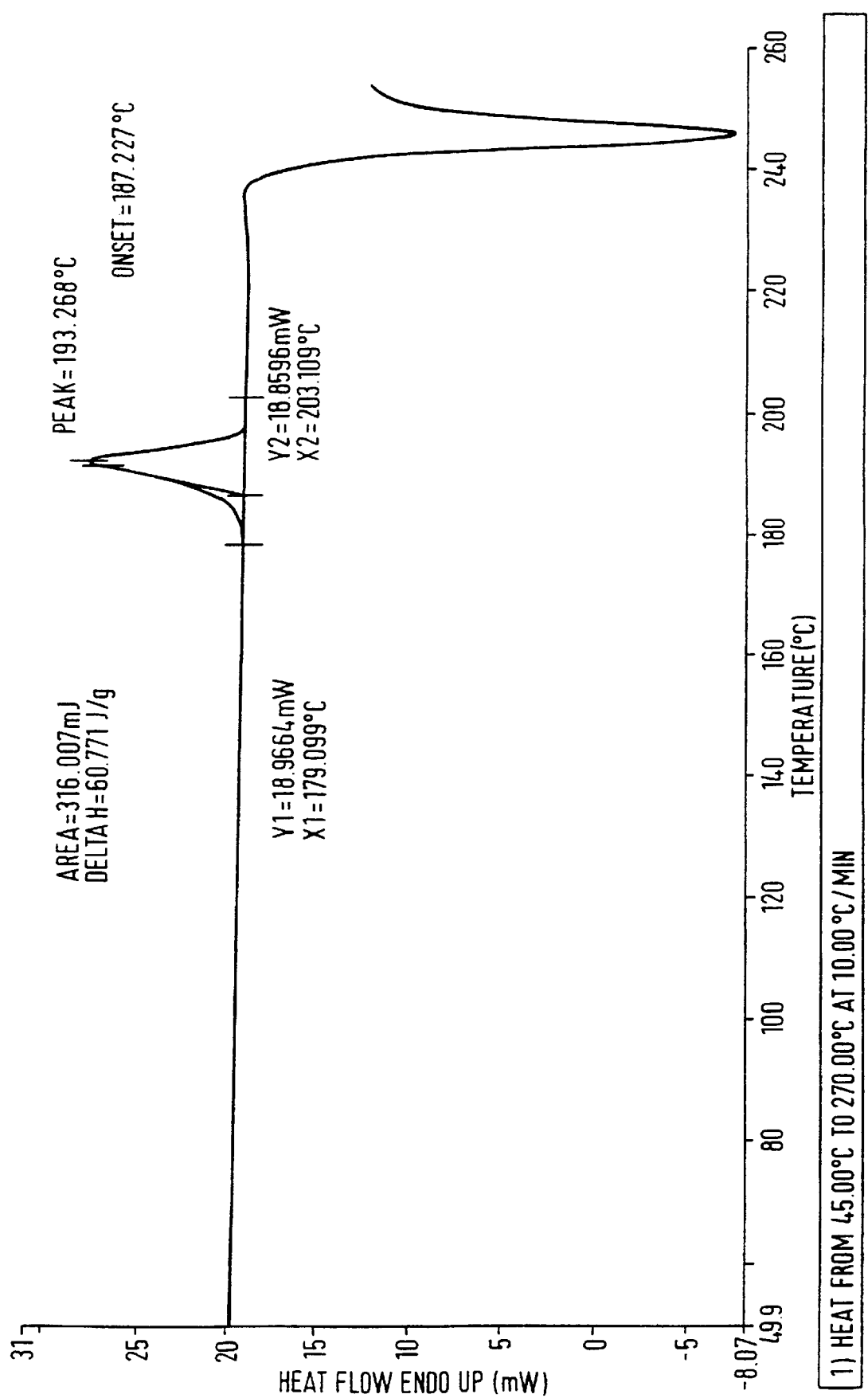
FIG. 6 DSC OF THE WHITE POLYMORPH

YELLOW POLYMORPH OF 5-AMINO-2,4,6-TRIIODO-N,N'-BIS(2-3-DIHYDROXYPROPY)-ISOPHTHALAMIDE

This application is a continuation of pending international application number PCT/GB98/01492 filed May 22, 1998 (if which the entire disclosure of the pending, prior application is hereby incorporated by reference), which itself is a continuation-in-part of U.S. provisional application number 60/049,176 filed Jun. 10, 1997, benefit of which is claimed under 35 U.S.C. 119(e).

This invention relates to the compound 5-amino-2,4,6-triiodo-N,N'-bis(2,3-dihydroxypropyl)-isophthalamide (hereinafter "compound A") and in particular to the yellow polymorphic form of compound A and its preparation and use.

Compound A is a key intermediate in the preparation of non-ionic X-ray contrast agents such as iohexol, iopentol, iodixanol, ioversol and iomeprol.

Compound A is available commiercially in a white form for instance from Fuji Chemical Industries, Ltd.

The preparation of compound A in a white form is disclosed for example in WO95/35122 (Mallinckrodt), eg. on page 6 thereof. Other publications, eg. Haavaldsen et al. in Acta Pharm. Suec. 20: 219–232 (1983), describe the preparation of compound A in a way in which the white form of compound A is produced.

Compound A however has now been found to exist in two polymorphic forms, a white form and a yellow form.

Polymorphism is a solid state phenomenon associated with the structure of the solid; different polymorphs of the same compound appear to involve different packings of the molecules within the solids.

We have now found that in large scale production of compound A the yellow polymorphic form has advantages over the white polymorphic form in terms of efficiency of the crystallisation, filtration and drying steps. In any large scale multistep synthetic production of a chemical drug substance, increased efficiency in any of the synthetic steps is reflected by increased efficiency of the overall process.

The white and yellow polymorphs of compound A have different infrared spectra and have characteristically different powder X-ray diffraction patterns. They may also be distinguished from each other by DSC and by colour assessment. Thus in particular the white polymorph in DSC has a peak melting temperature at about 193–196° C., while the yellow polymorph has a peak melting temperature in the range of about 247 to 252° C. Moreover the white polymorph is characterised over the yellow polymorph by having a sharp peak in the ir spectrum at 999 $cm^{-1}$.

Thus in one aspect the invention provides 5-amino-2,4,6-triiodo-N,N'-bis(2,3-dihydroxypropyl)-isophthalamide in its yellow polymorphic form.

In another aspect the invention provides 5-amino-2,4,6-triiodo-N,N'-bis(2,3-dihydroxypropyl)-isophthalamide in a form which in differential scanning calorimetry has a peak melting temperature in the range of about 247 to 252° C.

In a further aspect the invention provides 5-amino-2,4,6-triiodo-N,N'-bis(2,3-dihydroxypropyl)-isophthalamide in a form characterised by a diffuse reflectance infrared spectrum showing the following main peaks: 3330, 3244, 2929, 1641, 1564, 1402, 1277, 1228, 1115, 1032, 957, 690, 631 and 440 $cm^{-1}$. Moreover this infrared spectrum has at 999 $cm^{-1}$ either no peak, a shoulder, or a peak of low intensity, as compared to the characteristic high and sharp peak at 999 $cm^{-1}$ found in the equivalent infrared spectrum of the white polymorph. The diffuse reflectance infrared spectrum may be measured using a sample ground with KBr.

In a still further aspect the invention provides 5-amino-2,4,6-triiodo-N,N'-bis (2,3-dihydroxypropyl)-isophthalamide in a form characterised by the following X-ray powder diffraction pattern:

| d (Å) | I | d (Å) | I | d (Å) | I |
|---|---|---|---|---|---|
| 15.66 | w | 4.27 | s | 2.82 | w |
| 13.79 | w | 4.24 | m | 2.78 | m |
| 12.90 | s | 4.16 | m | 2.72 | w |
| 8.59 | vw | 4.11 | m | 2.69 | w |
| 8.25 | m | 4.00 | m | 2.62 | vw |
| 7.93 | w | 3.87 | m | 2.58 | w |
| 7.18 | w | 3.83 | w | 2.56 | w |
| 7.05 | vw | 3.58 | m | 2.52 | vw |
| 6.42 | s | 3.51 | w | 2.50 | vw |
| 6.30 | vwd | 3.44 | wd | 2.45 | vwd |
| 6.17 | w | 3.35 | vwd | 2.41 | vw |
| 5.84 | vw | 3.30 | vwd | 2.39 | vw |
| 5.71 | vwd | 3.23 | vwd | 2.35 | w |
| 5.53 | vw | 3.20 | w | 2.30 | wd |
| 5.25 | vwd | 3.18 | w | 2.23 | w |
| 5.01 | w | 3.04 | vw | | |
| 4.89 | w | 3.01 | w | | |
| 4.62 | m | 2.93 | vwd | | |
| 4.54 | vw | 2.92 | w | | |
| 4.45 | vwd | 2.85 | w | | |

(where w = weak, m = medium, s = strong, v = very and d = diffuse).

The mean crystal size of the yellow polymorph of compound A (as measured by particle sizing) is desirably in the range 150 to 500 μm, preferably 200 to 400 μm.

The yellow polymorph of compound A may be produced by cooling an aqueous solution of compound A at a rate of less than 7 C°/hour, eg. in the crystallisation step described on page 8 of GB-A-1548594 and on page 225 of Haavaldsen et al. (supra). It is the slow cooling rate that appears to result in the formation of the yellow polymorph rather than the white polymorph.

Thus viewed from a further aspect the invention provides a process for the preparation of 5-amino-2,4,6-triiodo-N,N'-bis(2,3-dihydroxypropyl)-isophthalamide in its yellow polymorphic form, said process comprising cooling a solution of 5-amino-2,4,6-triiodo-N,N'-bis(2,3-dihydroxypropyl)-isophthalamide, preferably an aqueous solution (eg. where the solvent is water or a mixture of water with a miscible cosolvent such as isopropanol), characterised in that cooling is effected at less than 7° C./hour (preferably at less than 6° C./hour and more preferably at less than 5° C./hour) during the period of precipitation of the 5-amino-2,4,6-triiodo-N,N'-bis(2,3-dihydroxypropyl)-isophthalamide.

The concentration of compound A in the starting solution is preferably 18 to 30% w/v, especially 22 to 26% w/v. Generally speaking the concentration requirement is essentially that the initial concentration should be higher than the saturation concentration at the end point of the cooling process, which will generally be in the range 0 to 30° C., preferably ambient temperature, eg. 18 to 25° C. The starting temperature for the solution will in normal practice be dictated by the temperature at the end point of the triiodination process by which compound A is prepared by reaction of an iodine halide (eg. $NaICl_2$) with the 2,4,6-unsubstituted precursor. This will generally be in the range 70–95° C. Nevertheless the yellow polymorph may be prepared by cooling a solution of compound A from a lower starting temperature, eg. in the range 40°–70° C.

In the process of the invention, the precipitation medium may be seeded with crystals of the yellow polymorph of compound A.

Following precipitation of compound A in its yellow polymorphic form, it will preferably be separated by filtration, washed (e.g. with alcohols (e.g. $C_{1-4}$ alkanols) or water or a mixture thereof), and dried (e.g. at 20 to 90° C.), before storage or further use.

Further use of the yellow polymorph will normally involve N-acylation, N-alkylation or dimerisation, eg. using procedures known in the art for the preparation of a 2,4,6-triiodinated-benzene ring containing X-ray contrast agent.

Viewed from a further aspect the present invention also provides the use of 5-amino-2,4,6-triiodo-N,N'-bis(2,3-dihydroxypropyl)-isophthalamide in its yellow polymorphic form in the production of an iodinated X-ray contrast agent, eg. an agent containing a 2,4,6-triiodo-N,N'-bis(2,3-dihydroxypropyl)-isophthalamide structure with a substituted nitrogen at the 5-position, for example an agent such as iohexol, iodixanol, iopentol, ioversol or iomeprol.

Such use according to the invention may simply involve the use of the yellow polymorph in synthetic procedures which previously have called for use of 5-amino-2,4,6-triiodo-N,N'-bis(2,3-dihydroxypropyl)-isophthalamide or for its white polymorph, eg. procedures as described by WO95/35122 (Mallinckrodt) for the preparation of ioversol, or by Haavaldsen et al. (supra) for the preparation of iohexol, or for the preparation of dimers as described in WO96/09285 (Nycomed).

For such further use, compound A may be entirely or substantially entirely in the yellow polymorph form, however some inclusion of the white polymorph and other polymorphs (e.g. with at least 50% of compound A, preferably at least 80%, more preferably at least 90%, and most preferably at least 95% by weight being in the yellow polymorphic form) is acceptable. Desirably the compound A used for such further use is at least 97% by weight pure.

The invention will now be described in further detail with reference to the following non-limiting Examples and the accompanying drawings, in which:

FIGS. 3 and 4 are powder X-ray diffraction patterns for the yellow and white polymorphs of compound A respectively;

FIGS. 5 and 6 are DSC traces for the yellow and white polymorphs-of compound A respectively.

EXAMPLE 1

Preparation of Yellow Polymorph of Compound A

A crude solution of 5-amino-2,4,6-triiodo-N,N'-bis(2,3-dihydroxypropyl)-isophthalamide (A) was prepared from 90 g 5-amino-N,N'-bis(2,3-dihydroxypropyl)isophthalamide HCl salt (prepared according to the method of Haavaldsen et al. in Acta. Pharm. Suec. 20: 219–232 (1983)). Iodine chloride, 3.45 equivalents to the isophthalamide, was added in 3 steps to the reaction mixture and kept at 60–85° C. pH was kept between 3–0.5 throughout the synthetic part of the reaction. To terminate the reaction 4–6.5 g of sodium metabisulphite was added at 70–80° C. to the crude solution of (A) and the mixture was basified to pH 3–5 with 50% caustic solution. Thereafter 2–3.5 g sodium dithionite was added and the batch was treated with 0.9 g seed at 78–82° C. and held at 80° C. for 2–3 hours to crystallize. The batch was cooled at 3° C. per hour until 15–30° C. and then further chilled and filtered.

The filtercake was washed with up to 50 ml water and then combined with a 10 ml rinse, filtered and washed 4 times with 50 ml water and two times with isopropanol.

The products was vacuum dried to yield 157 g product (A). The salt concentration in the final product was 0.02% w/w.

EXAMPLE 2

Infrared Spectra

Figure 1:
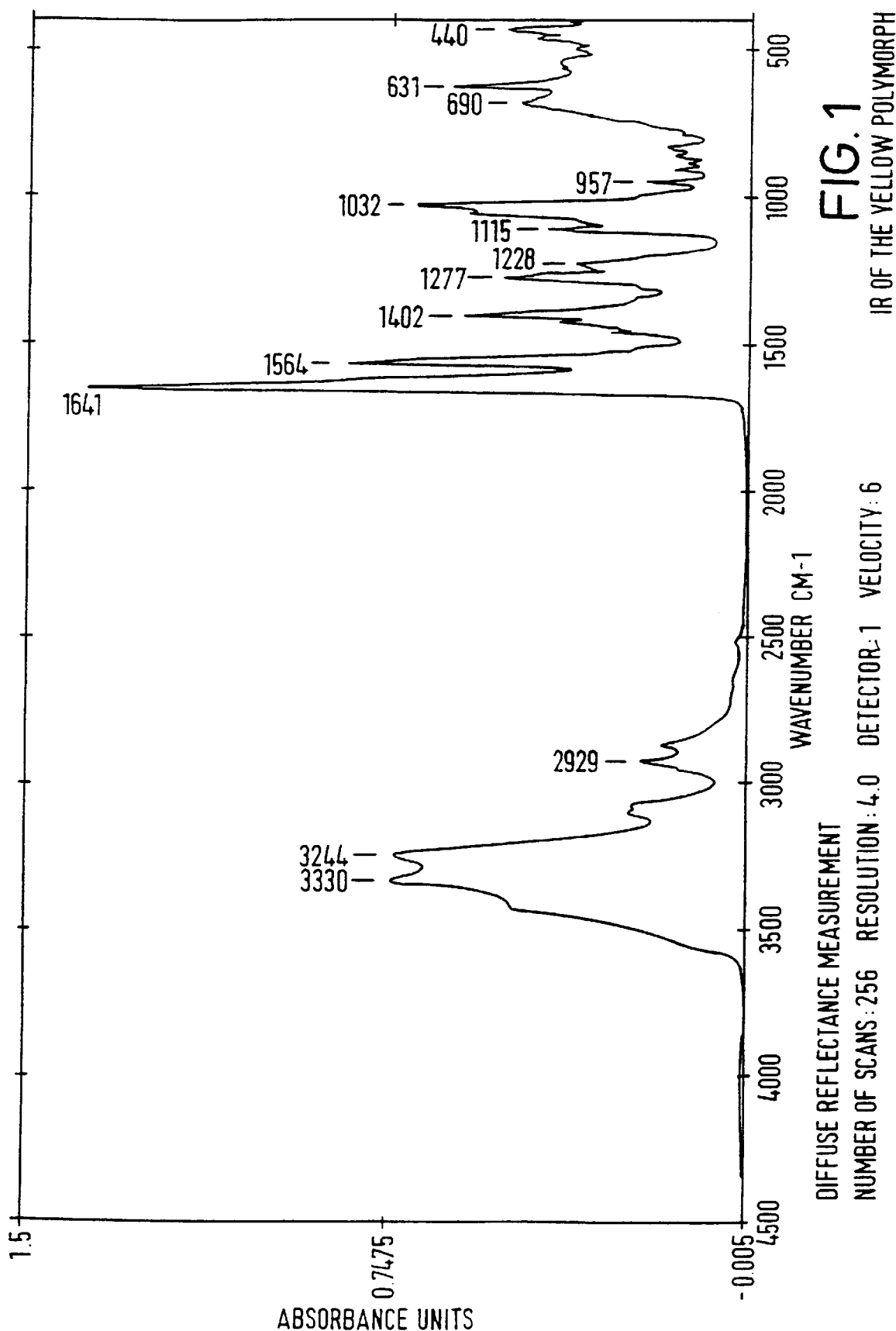
FIGS. 1 and 2 are infrared spectra for the yellow and white polymorphs of compound A respectively.
Figure 2:
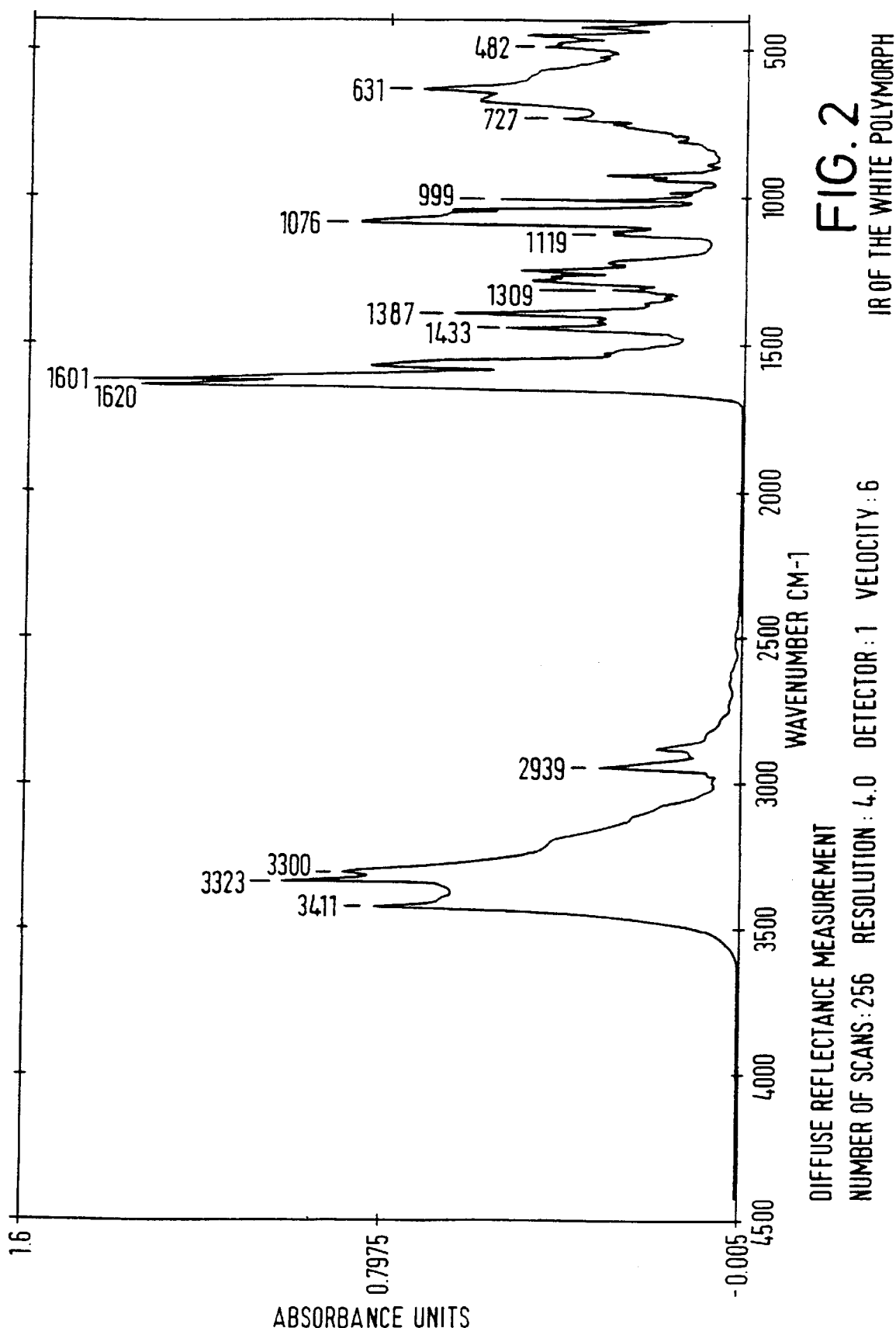

Characteristic peaks in the infrared spectra (diffuse reflectance measurement) for the yellow and white polymorph of compound A as shown in FIG. 1 and FIG. 2:

Yellow polymorph:
3330, 3244, 2929, 1641, 1564, 1402, 1277, 1228, 1115, 1032, 957, 690, 631, 440 cm$^{-1}$.

White polymorph:
3411, 3323, 3300, 2939, 1620, 1601, 1433, 1387, 1309, 1119, 1076, 999, 727, 631, 482 cm$^{-1}$.

EXAMPLE 3

Powder X-ray Diffraction

Samples of the yellow and white polymorphs of compound A were investigated with monochromatic CuKα radiation over the angle range of 2θ=3–60° using a SIEMENS D50000 diffractometer.

As shown in FIGS. 3 and 4, the following characteristic spacings and intensities are found for the yellow and white polymorph in terms of d spacings and relative intensities (I) is as follows
(s=strong, m=medium, w=weak, v=very, d=diffuse). Only d-values >2.20 Å are shown.

Yellow polymorph:

| d (Å) | I | d (Å) | I | d (Å) | I |
|---|---|---|---|---|---|
| 15.66 | w | 4.27 | s | 2.82 | w |
| 13.79 | w | 4.24 | m | 2.78 | m |
| 12.90 | s | 4.16 | m | 2.72 | w |
| 8.59 | vw | 4.11 | m | 2.69 | w |
| 8.25 | m | 4.00 | m | 2.62 | vw |
| 7.93 | w | 3.87 | m | 2.58 | w |
| 7.18 | w | 3.83 | w | 2.56 | w |
| 7.05 | vw | 3.58 | m | 2.52 | vw |
| 6.42 | s | 3.51 | w | 2.50 | vw |
| 6.30 | vwd | 3.44 | wd | 2.45 | vwd |
| 6.17 | w | 3.35 | vwd | 2.41 | vw |
| 5.84 | vw | 3.30 | vwd | 2.39 | vw |
| 5.71 | vwd | 3.23 | vwd | 2.35 | w |
| 5.53 | vw | 3.20 | w | 2.30 | wd |
| 5.25 | vwd | 3.18 | w | 2.23 | w |
| 5.01 | w | 3.04 | vw | | |
| 4.89 | w | 3.01 | w | | |
| 4.62 | m | 2.93 | vwd | | |
| 4.54 | vw | 2.92 | w | | |
| 4.45 | vwd | 2.85 | w | | |

White polymorph:

| d (Å) | I | d (Å) | I | d (Å) | I |
|---|---|---|---|---|---|
| 13.79 | s | 4.36 | vwd | 3.10 | vwd |
| 8.58 | m | 4.27 | vwd | 3.01 | wd |
| 8.35 | m | 4.16 | s | 2.92 | w |
| 7.39 | vwd | 4.09 | m | 2.89 | w |
| 7.07 | m | 4.01 | w | 2.84 | w |
| 6.84 | w | 3.92 | m | 2.76 | w |
| 6.21 | w | 3.80 | vwd | 2.72 | w |
| 6.04 | w | 3.69 | w | 2.66 | w |
| 5.73 | w | 3.57 | w | 2.57 | w |
| 5.52 | w | 3.52 | vw | 2.53 | vw |
| 5.25 | w | 3.43 | w | 2.44 | w |
| 4.90 | w | 3.40 | w | 2.40 | vw |

-continued

| d (Å) | I | d (Å) | I | d (Å) | I |
|---|---|---|---|---|---|
| 4.76 | vwd | 3.28 | w | 2.37 | w |
| 4.57 | vwd | 3.24 | w | 2.29 | vw |
| 4.45 | m | 3.15 | vwd | 2.27 | vw |
|  |  |  |  | 2.23 | w |

EXAMPLE 4

Melting Characteristics

According to DSC (Perkin Elmer DSC 7, temperature range 45° C.–270° C., heating rate 10° C./minute) the yellow and white polymorphs have the following melting characteristics, as shown in FIGS. 5 and 6:

Yellow polymorph:
Peak melting temperature in the range 247–252° C. (in this test the peak was at 249.7° C.).

White polymorph:
Peak melting temperature at about 193–196° C.

EXAMPLE 5

Manufacture of Iohexol yellow polymorphic compound a is used in the production of iohexol in a process similar to that described by haavaldsen et al. (supra)

What is claimed is:

1. 5-Amino-2,4,6-triiodo-N,N'-bis(2,3-dihydroxypropyl)-isophthalamide in a form which in differential scanning calorimetry has a peak melting temperature at about 247 to 252° C.

2. 5-Amino-2,4,6-triiodo-N,N'-bis(2,3-dihydroxypropyl)-isophthalamide in a form characterised by a diffuse reflectance infrared spectrum showing the following main peaks: 3330, 3244, 2929, 1641, 1564, 1402, 1277, 1228, 1115, 1032, 957, 690, 631 and 440 $cm^{-1}$.

3. 5-Amino-2,4,6-triiodo-N,N'-bis(2,3-dihydroxypropyl)-isophthalamide in a form characterised by the following X-ray powder diffraction pattern:

| d (Å) | I | d (Å) | I | d (Å) | I |
|---|---|---|---|---|---|
| 15.66 | w | 4.27 | s | 2.82 | w |
| 13.79 | w | 4.24 | m | 2.78 | m |
| 12.90 | s | 4.16 | m | 2.72 | w |
| 8.59 | vw | 4.11 | m | 2.69 | w |
| 8.25 | m | 4.00 | m | 2.62 | vw |
| 7.93 | w | 3.87 | m | 2.58 | w |
| 7.18 | w | 3.83 | w | 2.56 | w |
| 7.05 | vw | 3.58 | m | 2.52 | vw |
| 6.42 | s | 3.51 | w | 2.50 | vw |
| 6.30 | vwd | 3.44 | wd | 2.45 | vwd |
| 6.17 | w | 3.35 | vwd | 2.41 | vw |
| 5.84 | vw | 3.30 | vwd | 2.39 | vw |
| 5.71 | vwd | 3.23 | vwd | 2.35 | w |
| 5.53 | vw | 3.20 | w | 2.30 | wd |
| 5.25 | vwd | 3.18 | w | 2.23 | w |
| 5.01 | w | 3.04 | vw |  |  |
| 4.89 | w | 3.01 | w |  |  |
| 4.62 | m | 2.93 | vwd |  |  |
| 4.54 | vw | 2.92 | w |  |  |
| 4.45 | vwd | 2.85 | w |  |  |

(where w = weak, m = medium, s = strong, v = very and d = diffuse).

4. 5-Amino-2,4,6-triiodo-N,N'-bis(2,3-dihydroxypropyl)-isophthalamide as claimed in claim 1 having a mean particle size in the range 150 to 500 μm.

5. A process for the preparation of 5-amino-2,4,6-triiodo-N,N'-bis(2,3-dihydroxypropyl)-isophthalamide in its yellow polymorphic form, said process comprising cooling a solution of 5-amino-2,4,6-triiodo-N,N'-bis(2,3-dihydroxypropyl)-isophthalamide, characterised in that cooling is effected at less than 7 C°/hour during the period of precipitation of the 5-amino-2,4,6-triiodo-N,N'-bis(2,3-dihydroxypropyl)-isophthalamide.

* * * * *